United States Patent [19]

Beriger et al.

[11] Patent Number: 4,910,210
[45] Date of Patent: Mar. 20, 1990

[54] NEMATICIDAL COMPOSITIONS

[75] Inventors: Ernst Beriger, Allschwil, Switzerland; Wolfgang Eckhardt, Lörrach, Fed. Rep. of Germany

[73] Assignee: Ciba-Geigy Corp., Ardsley, N.Y.

[21] Appl. No.: 285,846

[22] Filed: Dec. 16, 1988

[30] Foreign Application Priority Data

Dec. 18, 1987 [CH] Switzerland .................. 4955/87

[51] Int. Cl.$^4$ .................. C07D 285/12; A01N 43/87
[52] U.S. Cl. .................. 514/363; 548/131; 548/142
[58] Field of Search .................. 548/142, 131; 514/363

[56] References Cited

U.S. PATENT DOCUMENTS

| | | | |
|---|---|---|---|
| 3,770,754 | 11/1973 | Parsons | 260/302 SD |
| 4,351,946 | 9/1982 | Toukon | 548/142 |
| 4,454,147 | 6/1984 | Di Menna et al. | 424/270 |
| 4,694,014 | 9/1987 | Ernst | 514/363 |

FOREIGN PATENT DOCUMENTS

| | | | |
|---|---|---|---|
| 1568552 | 5/1969 | France | 548/142 |
| 8607590 | 12/1986 | PCT Int'l Appl. | 548/142 |

Primary Examiner—Robert Gerstl
Attorney, Agent, or Firm—Edward McC. Roberts; George R. Dohmann

[57] ABSTRACT

Novel compounds of the formula

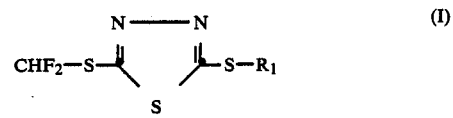

(I)

wherein
$R_1$ is $C_1$–$C_{12}$alkyl that is unsubstituted or substituted by halogen, phenyl, $C_1$–$C_3$alkoxy or by hydroxy, $C_1$–$C_3$alkyl that is substituted by carbonyl, O-alkylcarboxy, amino or by a heterocycle, unsubstituted or halo-substituted $C_3$–$C_7$cycloalkyl or unsubstituted cyclopropylmethyl, unsubstituted or halo-substituted $C_3$–$C_7$alkenyl, unsubstituted or halo-substituted $C_3$–$C_7$alkynyl, benzyl that is unsubstituted or mono-, di- or tri-substituted in the nucleus by $C_1$–$C_4$alkyl, halogen, nitro, cyano or by trifluoromethyl, or is the radical $R_2$—(O—CH$_2$—CH$_2$—)$_n$ wherein $R_2$ is hydrogen or $C_1$–$C_4$alkyl and n is a number from 1 to 3, as active ingredients for controlling nematodes that parasitise plants and for preventing damage to cultivated plants caused by nematode attack.

12 Claims, No Drawings

NEMATICIDAL COMPOSITIONS fluoroalkyl-1,3,4-thiadiazoles having nematicidal action, and in WO 86/07590 (PCT) the compound of formula V

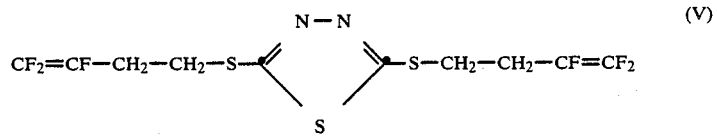

is described as a nematicide.

The present invention relates to novel substituted 2-thio-5-difluoromethylthio-1,3,4-thiadiazoles, to their preparation and to nematicidal compositions that contain at least one of those compounds as active ingredient. The invention also relates to the use of 2-thio-5-difluoromethylthio-1,3,4-thiadiazoles and compositions containing them for controlling nematodes, especially plant-destructive nematodes.

The 2-thio-5-difluoromethylthio-1,3,4-thiadiazoles according to the invention have the formula I

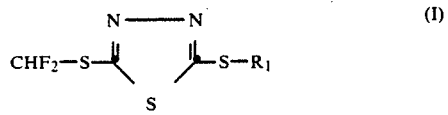

wherein
$R_1$ is $C_1$–$C_{12}$alkyl that is unsubstituted or substituted by halogen, phenyl, $C_1$–$C_3$alkoxy or by hydroxy, $C_1$–$C_3$alkyl that is substituted by carbonyl, O-alkylcarboxy, amino or by a heterocycle, unsubstituted or halo-substituted $C_3$–$C_7$cycloalkyl or unsubstituted cyclopropylmethyl, unsubstituted or halo-substituted $C_3$–$C_7$alkenyl, unsubstituted or halo-substituted $C_3$–$C_7$alkynyl, benzyl that is unsubstituted or mono-, di- or tri-substituted in the nucleus by $C_1$–$C_4$alkyl, halogen, nitro, cyano or by trifluoromethyl, or is the radical $R_2$—(O—$CH_2$—$CH_2$—)n wherein $R_2$ is hydrogen, or unsubstituted or hydroxy-substituted $C_1$–$C_4$alkyl and n is a number from 1 to 3.

Alkyl as an independent radical and as part of another group, such as alkoxy or O-alkylcarboxy, shall be understood as being straight-chain or branched-chain alkyl groups. Such groups include methyl, ethyl and normal and isomeric propyl, butyl and pentyl groups. Halo-substituted alkyl is a mono- to per-halogenated alkyl radical, for example $CHCl_2$, $CH_2F$, $CCl_3$, $CH_2Cl$, $CHFCH_3$, $CH_2CH_2Br$, $CF_2CF_3$, $C_2Cl_5$, $CH_2Br$, $CHBrCl$ etc., preferably $CHF_2$. Alkenyl is, for example, 1-propenyl, allyl, 1-butenyl, 2-butenyl or 3-butenyl and chains having several double bonds. Alkynyl is, for example, 2-propynyl, 1-butynyl, 2-butynyl, 4-pentynyl, etc.. Halogen is fluorine, chlorine, bromine or iodine, preferably fluorine, chlorine or bromine.

Cycloalkyl shall be understood as being cyclopropyl, cyclopentyl, cyclohexyl and cycloheptyl. The heterocycles include furan, thiophene, oxazole and oxadiazole.

Thiadiazole derivatives that are described as being nematicidally active are already known. For example, U.S. Pat. No. 3,770,754 discloses such compounds in which the hetero atoms are in the 1,2,4-position, while U.S. Pat. No. 4,454,147 describes 1,3,4-thiadiazole derivatives in which, as compared with the compounds according to the invention, the heterocycle is substituted by a chlorine atom instead of by mercapto groups. Furthermore, EP-A 217 747 discloses 5-phenyl-2-

As nematicides, these known compounds have hitherto been unable fully to satisfy the demands made of them in practice. The compounds of formula I according to the invention have a distribution coefficient (log P) that is favourable for soil application, and also a sufficiently high degree of water-solubility.

With the provision of the compounds of formula I according to the invention, it is now possible to make a valuable contribution to controlling plant nematodes which cause considerable agricultural damage to plants. In this manner, harvest losses of cultivated plants, for example potatoes, cereals, beet crops, rape, cabbage, tobacco, soybeans, cotton and vegetables, and also damage caused in tree nurseries and to ornamentals can be inhibited over a prolonged period. The compounds according to the invention are distinguished especially by the feature that they effectively control soil nematodes that parasitise roots, for example those nematodes of the genera Heterodera and Globodera (cystogenic nematodes), Meloidogyne (root-knot nematodes) and also of the genera Radopholus, Pratylenchus, Tylenchulus, Longidorus, Trichodorus and Xiphinema. The nematode genera Ditylenchus (stem parasites), Aphelenchoides (leaf nematodes) and Anguina (blossom nematodes) can also be effectively controlled with the compounds according to the invention.

Preferably, the compounds of formula I are used for successfully controlling especially harmful nematode species of the genus Meloidogyne, for example Meloidogyne incognita, of the genus Heterodera, for example Heterodera glycines (soybean cyst nematodes), and of the genus Globodera, for example Globodera rostochiensis (potato cyst nematodes), as well as representatives of migrating endoparasites, for example Pratylenchus penetrans or Radopholus similis, and representatives of ectoparasites, for example Trichlodorus spp. and Xiphinema spp..

To control plant nematodes and for the preservation of plant health, the novel compounds may be used curatively, preventively or systemically. They have a broad spectrum of activity against the various nematode species and therefore meet the requirements made of them in practice. The nematicidal mode of action of the compounds of the invention is coupled in advantageous manner with their low phytotoxicity, whereby the generally desirable reduction of harm to the environment is especially accommodated.

Within the scope of the present invention, preferred 2-thio-5-difluoromethylthio-1,3,4-thiadiazoles are those in which $R_1$ is $C_1$–$C_4$alkyl that is unsubstituted or substituted by halogen, phenyl, $C_1$–$C_3$alkoxy or by hydroxy, $C_3$–$C_4$alkenyl, $C_3$–$C_4$alkynyl, or the methoxycarbonylmethyl, the acetonyl, the 2-dimethylaminoethyl, the 2-furanylmethyl, the 2-thienylmethyl, the 3-methyloxazol-5-ylmethyl, the 5-methyl-1,2,4-oxadiazol-3-ylmethyl radical or the radical $R_2$—$(OCH_2CH_2)_n$—.

Among the group, the 2-thio-5-difluoromethylthio-1,3,4-thiadiazoles that are especially preferred are those in which $R_1$ is unsubstituted or halo-substituted $C_1$-$C_3$alkyl, or is $C_3$alkenyl or $C_3$alkynyl, or benzyl that is unsubstituted or mono- or di-substituted in the nucleus by halogen.

Of this group, attention is drawn to 2,5-bis(difluoromethylthio)-1,3,4-thiadiazole as one of the important individual compounds.

Compounds of formula I are prepared according to the invention by (a) reacting the 2,5-dimercapto-1,3,4-thiadiazole of formula II in a solvent first with a halogen compound of formula III, wherein $R_1$ is as defined in claim 1 and X is chlorine or bromine, in the presence of a base to form the 5-mercapto-1,3,4-thiadiazole derivative of formula IV, then converting the resulting intermediate of formula IV in a solvent with difluorochloromethane in the presence of a base into the end product of formula I:

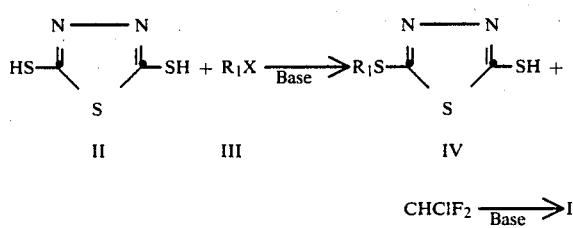

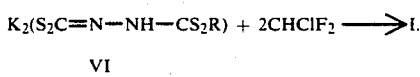

or (b) reacting a compound of formula VI in a solvent with difluorochloromethane to form the end product of formula I analogously to the method described in "Zeitschrift für anorganishe und allgemeine Chemie" (533 (1986) 99–108):

$$K_2(S_2C=N-NH-CS_2R) + 2CHClF_2 \longrightarrow I.$$

VI

Suitable solvents for the preparation of the intermediate of formula IV according to variant (a) are aliphatic and aromatic hydrocarbons, such as benzene, toluene, petroleum ether, alcohols, for example methanol, ethanol, isopropanol or butanol, ketones, such as acetone, diethyl ketone, methyl ethyl ketone, ethers and ethereal compounds, such as dialkyl ethers (diethyl ether, diisopropyl ether, tert.-butyl methyl ether etc.), anisole, dioxane, tetrahydrofuran, aliphatic and aromatic halogenerated hydrocarbons, such as chlorobenzene, methylene chloride, chloroform, ethylene chloride, carbon tetrachloride, tetrachloroethylene and, very generally, mixtures of such solvents with one another.

Suitable bases for this stage are organic and inorganic bases; for example ammonia, amines, such as triethylamine, triallylamine; and hydroxides of alkali and alkaline earth metals, such as NaOH, KOH, Ca(OH)$_2$.

Suitable solvents or diluents for the preparation of the compound according to the invention from the intermediate of formula IV are, for example, ethers and ethereal compounds, such as dialkyl ethers, dioxane, tetrahydrofuran, optionally in the form of aqueous mixtures.

Suitable bases for this stage are inorganic bases, and also oxides, hydroxides, carbonates and hydrogen carbonates of alkali and alkaline earth metals, preferably NaOH and KOH.

Suitable for the preparation of the compounds of the invention according to variant (b) are polar solvents, such as alcohols, and also dimethylformamide or dimethyl sulfoxide.

The reaction temperatures in the preparation processes are from 0° to 90° C., preferably from 20° to 60° C. The pressure conditions in the course of the reaction are to be from 1 to 20 bar, preferably 1 bar.

The starting compounds of formulae II and V are known, J. Org. Chem. 21 497–499, (1956) and Acta Chem. Scan. 15 1295–1302 (1961), respectively.

The invention also relates to compositions, for controlling plant-destructive nematodes and for protecting plants from attack by nematodes, that contain the compounds of formula I.

In addition, the present invention also includes the preparation of nematicidal compositions, which comprises homogeneously mixing compounds of formula I with one or more of the carriers and adjuvants described herein.

Also included is a method of treating plants, which comprises applying thereto the compounds of formula I or the novel compositions.

A preferred method of applying a compound of formula I or a nematicidal composition containing at least one of those compounds, is incorporation into the soil, which comprises treating the locus of the plants with a liquid or solid formulation.

The compounds of formula I can, however, also be applied to seeds (dressing/coating) either by impregnating the seeds with a liquid formulation of the active ingredient or by coating them with a solid formulation. In special cases, other methods of application are also possible, for example selective treatment of the plant stems, buds or leaves.

The compounds of formula I are normally applied in the form of compositions and can be applied to the crop area or plant to be treated, simultaneously or in succession, with further compounds. These further compounds can also include other substances applied in agriculture which are used to increase production by promoting growth of useful plants. Examples of such substances are fertilisers, herbicides, insecticides, fungicides, molluscicides, inter alia, or mixture of several of these preparations, if desired together with further carriers, surfactants or other application-promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

The compounds of formula I are used in unmodified form or, preferably, together with the adjuvants conventionally employed in the art of formulation. They are formulated in known manner e.g. to emulsifiable concentrates, directly sprayable or dilutable solutions, dilute emulsions, wettable powders, soluble powders, dusts, or are formulated to granulates by encapsulation in e.g. polymer substances. As with the nature of the compositions, the methods of application, such as spraying, atomising, scattering or pouring, are chosen in accordance with the intended objectives and the prevailing circumstances. Advantageous rates of application are normally from 500 g to 6 kg of active ingredient (a.i.) per hectare, preferably from 1 to 4 kg a.i./ha.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil. Mention may also be made of fatty acid methyllaurin salts and modified and unmodified phospholipids.

More frequently, however, so-called synthetic surfactants are used, especially fatty sulfonates, fatty sulfates, sulfonated benzimidazole derivatives or alkylsulfonates.

The fatty alcohol sulfonates or sulfates are usually in the form of alkali metal salts, alkaline earth metal salts or unsubstituted or substituted ammonium salts and contain a $C_8$–$C_{22}$-alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethyleneethanol, polyethylene glycol and octylphenoxypolyethoxyethanol.

Fatty acids esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$-alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described, inter alia, in the following publications:

"Mc Cutcheon's Detergents and Emulsifiers Annual" MC Publishing Corp., Ridgewood, N.J., 1979;

Dr. Helmut Stache "Tensid-Taschenbuch", Carl Hanser Verlag Munich/Vienna.

The agrochemical compositions usually contain 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also contain further auxiliaries such as stabilizers, antifoams, viscosity regulators, binders, tackifiers as well as fertilisers or other active ingredients for obtaining special effects.

The present invention relates also to such agrochemical compositions.

The following Examples serve to illustrate the invention in more detail and do not constitute a limitation thereof.

1. PREPARATION EXAMPLES

PREPARATION EXAMPLE 1.1

Preparation of 2,5-bis(difluoromethylthio)-1,3,4-thiadiazole 2 g of potassium hydroxide are dissolved in 24 ml of water, and then 9 g of the dipotassium salt of 2,5-dimercapto-1,3,4-thiadiazole, 120 ml of dioxane, 0.4 g of potassium iodide and 0.2 g of tetrabutylammonium bromide are added to the solution with stirring. Difluorochloromethane is then slowly introduced into the solution over a period of 3 hours at 40° C. with vigorous stirring. The solvent is then evaporated off in vacuo, the residue is taken up in methylene chloride and the solution is washed in succession with water and then 1N sodium hydroxide solution and, after distilling off the solvent, 3.4 g of the desired product, $n_D^{23}=1.5452$, are obtained. The distribution coefficient for soil application is log P=1.7. In contrast, compound V already known from the prior art has a value of log P=5.0 which is very much less favourable for soil application.

The following compounds according to the invention can be prepared analogously to the above Preparation Example and the processes described hereinbefore. The compounds listed below serve to illustrate the present invention and do not constitute a limitation thereof.

TABLE 1

R—S—⟨N=N⟩—SCHF₂
    \S/

| Comp. No. | R | Physic. data |
|---|---|---|
| 1 | CH₃— | $n_D^{25}$: 1,6067 |
| 2 | C₂H₅ | |
| 3 | C₃H₇(n)- | |
| 4 | C₃H₇(i)- | $n_D^{25}$: 1,5682 |
| 5 | C₄H₉(n)- | |
| 6 | ClCH₂— | |
| 7 | F₂CH— | $n_D^{23}$: 1,5452 |
| 8 | CF₃CF₂— | oil |
| 9 | CF₃CHFCF₂— | |
| 10 | CF₂=CFCH₂CH₂— | $n_D^{25}$: 1,5278 |
| 11 | CH₂=C(Br)—CH₂— | oil |
| 12 | CH₂=CH—CH₂— | $n_D^{25}$: 1,5950 |
| 13 | HC≡C—CH₂— | $n_D^{25}$: 1,6139 |
| 14 | cyclopropyl-CH₂— | oil |
| 15 | 4-Br-C₆H₄-CH₂— | oil |
| 16 | 4-Cl-C₆H₄-CH₂— | $n_D^{25}$: 1,6293 |
| 17 | 2-Cl-C₆H₄-CH₂— | $n_D^{25}$: 1,6259 |

TABLE 1-continued

R—S—⟨N=N⟩—SCHF₂
    \S/

| Comp. No. | R | Physic. data |
|---|---|---|
| 18 | 2-Cl-C₆H₄-CH₂— | $n_D^{25}$: 1,6355 |
| 19 | 2,6-Cl₂-C₆H₃-CH₂— | $n_D^{25}$: 1,6351 |
| 20 | 4-CH₃O-C₆H₄-CH₂— | semi-solid |
| 21 | 4-O₂N-C₆H₄-CH₂— | |
| 22 | furfuryl-CH₂— | $n_D^{25}$: 1,6138 |
| 23 | thienyl-CH₂— | $n_D^{25}$: 1,6503 |
| 24 | C₆H₅-CH(CH₃)— | $n_D^{23}$: 1,6100 |
| 25 | 2,4,6-Cl₃-C₆H₂-CH₂— | |
| 26 | 4-CF₃-C₆H₄-CH₂— | $n_D^{25}$: 1,6554 |
| 27 | 4-H₃C-C₆H₄-CH₂— | |

TABLE 1-continued

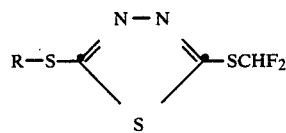

| Comp. No. | R | Physic. data |
|---|---|---|
| 28 | 3,4,5-(CH$_3$O)$_3$-C$_6$H$_2$-CH$_2$- | semi-solid |
| 29 | 4-CF$_3$-C$_6$H$_4$-CH$_2$- | wax |
| 30 | 4-NC-C$_6$H$_4$-CH$_2$- | m.p.: 57–59° C. |
| 31 | 2-F-C$_6$H$_4$-CH$_2$- | n$_D^{25}$: 1,6059 |
| 32 | 3-F-C$_6$H$_4$-CH$_2$- | n$_D^{25}$: 1,6061 |
| 33 | 4-F-C$_6$H$_4$-CH$_2$- | n$_D^{25}$: 1,6620 |
| 34 | 4-(CH$_3$)$_3$C-C$_6$H$_4$-CH$_2$- | n$_D^{25}$: 1,5875 |
| 35 | CH$_3$OOCCH$_2$- | n$_D^{25}$: 1,5760 |
| 36 | CH$_3$COCH$_2$- | m.p.: 48–50° C. |
| 37 | 3-methyl-isoxazol-5-yl-CH$_2$- | semi-solid |
| 38 | 3-methyl-1,2,4-oxadiazol-5-yl-CH$_2$- | n$_D^{25}$: 1,5905 |
| 39 | (CH$_3$)$_2$NCH$_2$CH$_2$- | oil |
| 40 | CH$_3$OCH$_2$CH$_2$- | n$_D^{25}$: 1,5687 |
| 41 | HOCH$_2$CH$_2$OCH$_2$CH$_2$- | |
| 42 | CH$_3$CH$_2$OCH$_2$CH$_2$- | |
| 43 | ClCH$_2$CH$_2$- | n$_D^{25}$: 1,6023 |

TABLE 1-continued

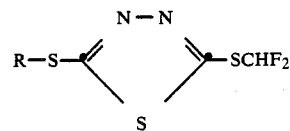

| Comp. No. | R | Physic. data |
|---|---|---|
| 44 | CH$_3$OCH$_2$CH$_2$OCH$_2$CH$_2$- | n$_D^{25}$: 1,5500 |
| 45 | CH$_3$CH$_2$OCH$_2$CH$_2$- | |
| 46 | CH$_3$CH$_2$OCH$_2$CH$_2$OCH$_2$CH$_2$- | |
| 47 | CH$_3$CH$_2$OCH$_2$CH$_2$OCH$_2$CH$_2$OCH$_2$CH$_2$- | |
| 48 | n-C$_4$H$_9$OCH$_2$CH$_2$OCH$_2$CH$_2$OCH$_2$CH$_2$- | |
| 49 | 2,6-Cl$_2$-C$_6$H$_3$-CH$_2$- | n$_D^{25}$: 1,6353 |
| 50 | CF$_3$CH$_2$- | |

2. FORMULATION EXAMPLES FOR LIQUID ACTIVE INGREDIENTS OF FORMULA I
(throughout, percentages are by weight)

| 2.1 Emulsifiable concentrates | (a) | (b) | (c) |
|---|---|---|---|
| a compound of Tables 1 to 3 | 25% | 40% | 50% |
| calcium dodecyl benzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 2.2 Solutions | (a) | (b) | (c) | (d) |
|---|---|---|---|---|
| a compound of Tables 1 to 3 | 80% | 10% | 5% | 95% |
| ethylene glycol monomethyl ether | 20% | — | — | — |
| polyethylene glycol (mol. wt. 400) | — | 70% | — | — |
| N—methyl-2-pyrrolidone | — | 20% | — | — |
| epoxidised coconut oil | — | — | 1% | 5% |
| petroleum fraction (boiling range 160–190° C.) | — | — | 94% | — |

These solutions are suitable for application in the form of microdrops.

| 2.3 Granulates | (a) | (b) |
|---|---|---|
| a compound of Tables 1 to 3 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4 Dusts | (a) | (b) |
|---|---|---|
| a compound of Tables 1 to 3 | 2% | 5% |
| highly dispersed silicic acid | 1% | 5% |

| 2.4 Dusts | (a) | (b) |
|---|---|---|
| talcum | 97% | — |
| kaolin | — | 90% |

Ready-for-use dusts are obtained by intimately mixing the carriers with the active ingredient.

FORMULATION EXAMPLES FOR SOLID ACTIVE INGREDIENTS OF FORMULA I
(throughout, percentages are by weight)

| 2.5 Wettable powders | (a) | (b) | (c) |
|---|---|---|---|
| a compound of Tables 1 to 3 | 25% | 50% | 75% |
| sodium lignosulfonate | 5% | 5% | — |
| sodium lauryl sulfate | 3% | — | 5% |
| sodium diisobutyl naphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.6 Emulsifiable concentrate | |
|---|---|
| a compound of Tables 1 to 3 | 10% |
| octylphenol polyethylene glycol ether (4–5 moles of ethylene oxide) | 3% |
| calcium dodecyl benzenesulfonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

| 2.7 Dusts | (a) | (b) |
|---|---|---|
| a compound of Tables 1 to 3 | 5% | 8% |
| talcum | 95% | — |
| kaolin | — | 92% |

Ready-for-use dusts are obtained by mixing the active ingredient with the carriers, and grinding the mixture in a suitable mill.

| 2.8 Extruder granulate | |
|---|---|
| a compound of Tables 1 to 3 | 10% |
| sodium lignosulfonate | 2% |
| carboxymethylcellulose | 1% |
| kaolin | 87% |

The active ingredient ia mixed and ground with the adjuvants, and the mixture is subsequently moistened with water. The mixture is extruded and then dried in a stream of air.

| 2.9 Coated granulate | |
|---|---|
| a compound of Tables 1 to 3 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 2.10 Suspension concentrate | |
|---|---|
| a compound of Tables 1 to 3 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

BIOLOGICAL EXAMPLE 3.1 ACTION AGAINST MELOIDOGYNE INCOGNITA ON TOMATO PLANTS

Eggs of Meloidogyne incognita are mixed into sand. This mixture is then put into 200 ml clay pots (5000 eggs per pot). On the same day a three-week-old tomato plant is planted in each pot and the formulated test compound is introduced into the pots by drench application (0.0006% of active ingredient, based on the volume of the soil). The potted plants are then placed in a greenhouse at a temperature of $26 \pm 1°$ C. and a relative humidity of 60%. After 4 weeks, evaluation is made by examining the plants for root-knot formation in accordance with the so-called Root-Knot Index.

Compounds of Table 1 exhibit good activity against Meloidogyne incognita in that they substantially reduce root-knot formation. On the other hand, untreated and infected control plants exhibit severe root-knot formation (=100%). Thus, in this test, for example compound no. 7 inhibits root-knot formation almost completely (0–10% residual attack).

What is claimed is:

1. 2-Thio-5-difluoromethylthio-1,3,4-thiadiazoles of formula I $$\text{CHF}_2-S-\underset{S}{\underset{\|}{\overset{N-N}{\underset{\|}{\diagup\diagdown}}}}-S-R_1 \quad (I)$$

wherein $R_1$ is $C_1$–$C_4$alkyl that is unsubstituted or substituted by halogen, phenyl, $C_1$–$C_3$alkoxy or hydroxy, $C_3$–$C_4$alkenyl, $C_3$–$C_4$alkynyl, or the methoxycarbonylmethyl, the acetonyl, the 2-dimethylaminoethyl, the 2-furanylmethyl, the 2-thienylmethyl, the 3-methyloxazol-5-ylmethyl, the 5-methyl-1,2,4-oxadiazol-3-ylmethyl radical or the radical $R_2$—$(OCH_2CH_2)_n$— wherein $R_2$ is hydrogen or unsubstituted or hydroxy-substituted $C_1$–$C_4$alkyl and n is a number from 2 to 3.

2. 2-thio-5-difluoromethylthio-1,3,4-thiadiazoles according to claim 1, wherein $R_1$ is unsubstituted or halo-substituted $C_1$–$C_3$alkyl, or is $C_3$alkenyl or $C_3$alkynyl, or benzyl that is unsubstituted or mono- or di-substituted in the nucleus by halogen.

3. 2,5-bis(difluoromethylthio)-1,3,4-thiadiazole.

4. A pesticidal composition for controlling or preventing attacks on plants by nematodes, which contains an active ingredient a pesticidally effective amount of at least one compound of formula I according to claim 1.

5. A composition according to claim 4, which contains as active ingredient at least one compound of formula I according to claims 3.

6. A compositiona according to claim 5, which contains 2,5-bis(difluoromethylthio)-1,3,4-thiadiazole as active ingredient.

7. A composition according to claim 4, which contains 0.1 to 99% of a compound of formula I, 99.9 to 1% of a solid or liquid adjuvant and 0 to 25% of a surfactant.

8. A composition according to claim 7, which contains 0.1 to 95% of a compound of formula I, 99.8 to 5% of a solid or liquid adjuvant and 0.1 to 25% of a surfactant.

9. A method of controlling or preventing attacks on cultivated plants by nematodes, whch comprises applying a compound of formula I according to claim 1 to the plant or the locus thereof.

10. A method according to claim 9, wherein the nematodes are species that parasitise plants.

11. A method according to claim 10 against nematodes of the genus Meloidogyne, Heterodera or Globodera.

12. A method of controlling or preventing attacks on cultivated plants by nematodes, which comprises applying a compound of claim 3 to the plant or the locus thereof.

* * * * *